United States Patent [19]

Shelby et al.

[11] Patent Number: 5,519,047
[45] Date of Patent: May 21, 1996

[54] IMMUNOMODULATORY ACTIVITY OF EXOGENOUS MELATONIN FOLLOWING TRAUMATIC INJURY

[75] Inventors: Jane Shelby, Park City; Harold C. Nielson, Salt Lake City, both of Utah

[73] Assignee: University of Utah Research Foundation, Salt Lake City, Utah

[21] Appl. No.: 230,543

[22] Filed: Apr. 20, 1994

[51] Int. Cl.$^6$ .................................................. A61K 31/40
[52] U.S. Cl. ........................................... 514/419; 514/885
[58] Field of Search ..................................... 514/419, 885

[56] References Cited

U.S. PATENT DOCUMENTS 4,855,325  8/1989  Naftchi ..................................... 514/634

OTHER PUBLICATIONS

CA 115:106637, Fraschini et al., 1990.
CA 116: 249055, Caroleo et al., 1992.
CA 117: 46488, Wang et al., 1992.
CA 108: 143860, Maestroni et al., 1988.
CA 121: 253426, Muscettola et al., 1994.

*Primary Examiner*—Kimberly Jordan
*Attorney, Agent, or Firm*—Thorpe North & Western

[57] ABSTRACT

A method of decreasing elevated levels of IL-6 and γ-IFN that are secreted in response to traumatic injury in a warm-blooded animal is disclosed, comprising the step of administering an effective amount of melatonin to the animal. The melatonin should be administered so as to provide a peak amount of circulating melatonin at a time in the animal's daily cycle when endogenous melatonin reaches peak amounts. Elevated levels of IL-6 and γ-IFN are also decreased by exposing the animal to certain daily regimens of light and dark, such as 24 hours of dark. Cell-mediated immune response to a contact antigen is also enhanced by administration of exogenous melatonin.

10 Claims, 5 Drawing Sheets

IMMUNOMODULATORY ACTIVITY OF EXOGENOUS MELATONIN FOLLOWING TRAUMATIC INJURY

BACKGROUND OF THE INVENTION

This invention relates to a method of stimulating post-trauma immune response in warm-blooded animals including humans. More particularly, this invention relates to a method of regulating cytokine activity in vivo, moderating cytokine excesses in response to injury, and potentiating cellular response to enhance resistance to infection by administering exogenous melatonin.

Melatonin (N-acetyl-5-methoxytryptamine) is a neurohormone produced in and secreted by the pineal gland of humans and other warm-blooded animals. The highest levels of secreted melatonin occur during the dark period of a circadian light-dark cycle. This hormone is also found in the retina and the gut.

Melatonin is involved in the transduction of photoperiodic information and appears to modulate a variety of neural and endocrine functions in vertebrates, including the regulation of reproduction, body weight and metabolism in photoperiodic mammals, control of circadian rhythms, and modulation of retinal physiology. Retinal melatonin has been implicated in photoreceptor outer disc shedding and phagocytosis, in melanosome aggregation in pigment epithelium, and cone photoreceptor retinomotor movement. Of the various physiological processes that have been associated with melatonin, those best substantiated are its effects on sexual maturation, ovarian function, and chronobiological rhythms. J. Arendt, 8 Oxford Review of Reproductive Biology 266–320 (1986); M. Dubocovich, *Pharmacology and Function of Melatonin Receptors*, 2 FASEB J. 2765 (1988).

Exogenous melatonin administration has been found to synchronize circadian rhythms in rats. Cassone et al., 1 J. Biol. Rhythms 219 (1986). In humans, administration of melatonin has been used to treat jet-lag related sleep disturbances, considered to be caused by desynchronization of circadian rhythms. J. Arendt et al., 292 Br. Med. J. 1170 (1986).

Alterations in immune response following traumatic injury, including dysregulation of immune cell cytokine secretion, are a result of a dynamic neuroendocrine process reflecting the attempted adaptive response of an injured host. The most widely investigated component of this process of adaptation to a stressful challenge is the hypothalamic-pituitary-adrenal (HPA) axis, the activation of which results in the well known elevation of glucocorticoid levels in trauma patients. V. Vaughan et al., *Cortisol and Corticotropin in Burned Patients*, 22 J. Trauma 263 (1982). There is considerable evidence for the suppressive effects of glucocorticoid on immune function, which may play a role in trauma-associated immune suppression. T. Cupps & A. Fauci, *Corticosteroid-Mediated Immunoregulation in Man*, 65 Immunol. Rev. 134 (1982).

Recent work has revealed that other neural products associated with the stress response also have immune regulating activity, suggesting that both the nervous and immune systems use these signal molecules in adaptive responses. A. Dunn, *Recent Advances in Psychoneuroimmunology*, 3 Curr. Opinions in Psychiatry 103 (1990); R. Dantzer & K. Kelley, *Stress and Immunity: An Integrated View of Relationships between the Brain and Immune System*, 44 Life Sciences 1995 (1989); T. Roszman & S. Carlson, *Neurotransmitters and Molecular Signaling in the Immune Response*, in *Psychoneuroimmunology* 311–35 (R. Ader, D. Felten, N. Cohen eds., 2d ed., 1991). Neuropeptides influence immune reactivity by direct and indirect pathways, including tissue distribution, proliferative and synthetic responses, and cytotoxic activities of lymphocytes. Evidence for direct effects on immune response is strengthened by the discovery that immune cells possess receptors for these neural derived molecules. D. Carr & J. Blalock, *Neuropeptide Hormones and Receptors common to the Immune and Neuroendocrine Systems: Bidirectional Pathway of Intersystem Communication*, in *Psychoneuroimmunology* 573–88 (R. Ader, D. Felten, N. Cohen eds., 2d ed., 1991). These neural/immune system interactions may occur in a hormonal (via circulation), paracrine (released from nerves), or autocrine (produced by immune cells themselves) fashion.

Nerve mapping studies have revealed innervation of lymphoid organs, including the thymus, spleen, lymph nodes, and bone marrow, with evidence for secretion of neurotransmitters in the immediate lymphoid microenvironment. S. Felten a D. Felten, *Innervation of Lymphoid Tissue*, in *Psychoneuroimmunology* 27–61 (R. Ader, D. Felten, N. Cohen eds., 2d ed., 1991). Additionally, there is evidence that T cells produce ACTH, β-endorphin, and corticotropin-releasing hormone molecules that are identical to the neural product, thereby setting the stage for paracrine and autocrine delivery to immune cells of these regulatory molecules. E. Goetzl et al., *Production and Recognition of Neuropeptides by Cells of the Immune System*, in *Psychoneuroimmunology* 263–82 (R. Ader, D. Felten, N. Cohen eds., 2d ed., 1991); H. Besedovsky & A. Del Ray, *Physiological Implications of the Immune-Neuro-Endocrine Network*, in *Psychoneuroimmunology* 589–608 (R. Ader, D. Felten, N. Cohen eds., 2d ed., 1991).

Discoveries in neuroimmunologic research have also revealed that immune cell cytokine secretion is under neuroendocrine control. M. Caroleo et al., *Melatonin as Immunomodulator in Immunodeficient Mice*, 23 Immunopharmacology 81 (1992); V. Gobbo et al., *Pinealectomy Inhibits Interleukin-2 Production and Natural Killer Cell Activity in Mice*, 11 Int. N.J. Immunopharmacology 567 (1989); No Spector a E. Korneva, *Neurophysiology, Immunophysiology and Neuroimmunomodulation*, in *Psychoneuroimmunology* 449–73 (R. Ader, D. Felten, N. Cohen eds., 2d ed., 1991). However, understanding of the mechanisms responsible for central nervous system (CNS) regulation of immune response and cytokine production is incomplete, and very little in known about the role of this process in regulation of host immune response following trauma.

Melatonin appears to have immunostimulatory effects in models of stress. M. Caroleo et al., *Melatonin as Immunomodulator in Immunodeficient Mice*, 23 Immunopharmacology 81 (1992); V. Gobbo et al., *Pinealectomy Inhibits Interleukin-2 Production and Natural Killer Cell Activity in Mice*, 11 Int. N. J. Immunopharmacology 567 (1989); G. Maestroni et al., *Pineal Melatonin, Its Fundamental Immunoregulatory Role in Aging and Cancer*, 521 Ann. N.Y. Acad. Sci. 140 (1988). Recently it has been observed that disruption of light/dark cycles induces significant changes in the CNS, with subsequent alterations in several physiologic functions, including immune response. B. Radosevic-Stasic et al., *Immune Response of Rats after Pharmacologic Pinealectomy*, 5 Period Biol. 282 (1983); R. Wurtman & f. Waldhauser, *Melatonin in Humans*, J. Neural Transmission Supp. 21 (1986). Mediation of these changes appears to be linked to the pineal gland and melatonin. G. Maestroni et al., *Role of the Pineal Gland in Immunity: Circadian Synthesis and Release of Melatonin Modulates the Antibody Response* and *Antagonizes the Immunosuppressive Effect of Corticosterone*, 13 J. Neuroimmunol. 19 (1986); G. Maestroni & A. Conti, *Role of the Pineal Neurohormone Melatonin in the Psycho-Neuroendocrine-Immune Network*, in *Psychoneuroimmunology* 495–513 (R. Ader, D. Felten, N. Cohen eds., 2d ed., 1991). Melatonin is known to act at the hypothalamic level, W. Pierpaoli & Y. Changxian, *The Involvement of Pineal Gland and Melatonin in Immunity and Aging. I. Thymus-Mediated, Immunoreconstituting, and Antiviral Activity of Thyrotropin-Releasing Hormone*, 27 J. Neuroimmunol. 99 (1990), affecting thermoregulation and pituitary release of certain hormones, W. Pierpaoli & Y. Changxian, 27 J. Neuroimmunol. 99 (1990); J. Beck-Friis et al., *The Pineal Gland in Affective Disorders*, in *The Pineal Gland: Endocrine Aspects* 313–25 (G. Brown, S. Wainwright eds., 1985). The pineal gland and melatonin have been reported to exert an oncostatic effect on carcinogenesis and tumor growth, W. Regelson a W. Pierpaoli, *Melatonin: A Rediscovered Antitumor Hormone? Its Relation to Surface Receptors, Sex Steroid Metabolism, Immunologic Response, and Chronobiologic Factors in Tumor Growth and Therapy*, 5 Cancer Invest. 379 (1985), and neoplastic diseases have been associated with immune depression and altered plasma melatonin levels, P. Lissoni et al., *Endocrine Effects of a 24 Hour Intravenous Infusion of Interleukin-2 in the Immunotherapy of Cancer*, 10 Anticancer Res. 753 (1990); P. Lissoni et al., *Endocrine and Immune Effects of Melatonin Therapy in Metastatic Cancer Patients*, 25 Eur. J. Cancer. Clin. Oncol. 789 (1989); P. Lissoni et al., *Alterations of Pineal Gland and of T Lymphocyte Subsets in Metastatic Cancer Patients: Preliminary Results*, 3 J. Biol. Regulators and Homeostatic Agents 181 (1990). Administration of exogenous melatonin has been shown to enhance several immune parameters in normal and restraint-stressed mice. G. Maestroni et al., *Pineal Melatonin, Its Fundamental Immunoregulatory Role in Aging and Cancer*, 521 Ann. N.Y. Acad. Sci. 140 (1988). There have also been reports of melatonin-mediated up-regulation of T cell interleukin-2 (IL-2) production in mice that were immunodeficient because of extremes of age or cyclophosphamide therapy. M. Caroleo et al., *Melatonin as Immunomodulator in Immunodeficient Mice*, 23 Immunopharmacology 81 (1992). Similarly, pinealectomy was shown to inhibit IL-2 production and natural killer cell (NK) activity in mice, while administration of exogenous melatonin in pinealectomized mice restored IL-2 production and NK activity. V. Gobbo et al., *Pinealectomy Inhibits Interleukin-2 Production and Natural Killer Cell Activity in Mice*, 11 Int. N.J. Immunopharmacology 567 (1989). Thus, melatonin appears to exert immunoenhancing effects in several models of immunodeficiency. Additionally, peak plasma melatonin levels have been shown to be significantly depressed in burn patients, G. Vaughn et al., *Pineal Function in Burns: Melatonin Is Not a Marker for General Sympathetic Activity*, 2 J. Pineal Res. 1 (1985). Cytokine secretion alterations have been noted following injury, including decreases in IL-2, N. Moss et al., *Temporal Correlation of Impaired Immune Response after Thermal Injury with Susceptibility to Infection in a Murine Model*, 104 Surgery 882 (1988). The possible role for melatonin in immune function alterations following thermal injury has not been previously evaluated. Further, there is no evidence linking in vivo administration of exogenous melatonin to regulation of cytokines IL-6 and $\delta$-IFN.

OBJECTS AND SUMMARY OF THE INVENTION

It is an object of the present invention to provide a method of stimulating post-trauma immune response in warm-blooded animals including humans.

It is also an object of the invention to provide a method of regulating cytokine activity in vivo following stress, injury, or other trauma.

It is another object of the invention to provide a method of moderating cytokine excesses in response to injury or other trauma.

It is still another object of the invention to provide a method of potentiating cellular response to enhance resistance to infection.

It is yet another object of the invention to regulate cytokines IL-6 and $\delta$-IFN following trauma and, in particular, thermal injury.

These and other objects are accomplished by providing a method for decreasing elevated levels of IL-6 and $\delta$-IFN that are secreted in response to traumatic injury, such as thermal injury, in a warm-blooded animal, comprising the step of administering an effective amount of melatonin to the animal. The melatonin is preferably injected to provide a peak amount of circulating melatonin at a time in the animal's daily cycle when endogenous melatonin reaches peak amounts.

Elevated levels of IL-6 and $\delta$-IFN secreted in response to traumatic injury, such as thermal injury, can also be decreased by administering an effective regimen of exposure to light and dark. One such effective regimen is daily exposure to 24 hours of dark.

Elevated levels of IL-6 and $\delta$-IFN secreted in response to traumatic injury, such as thermal injury, can also be decreased by administering an effective amount of melatonin and an effective regimen of exposure to light and dark.

A method is also provided for enhancing cell-mediated immune response, such as from exposure to a contact antigen, in a warm-blooded animal that has received a traumatic injury, comprising the step of administering an effective amount of exogenous melatonin.

DETAILED DESCRIPTION OF THE INVENTION

Figure 1:
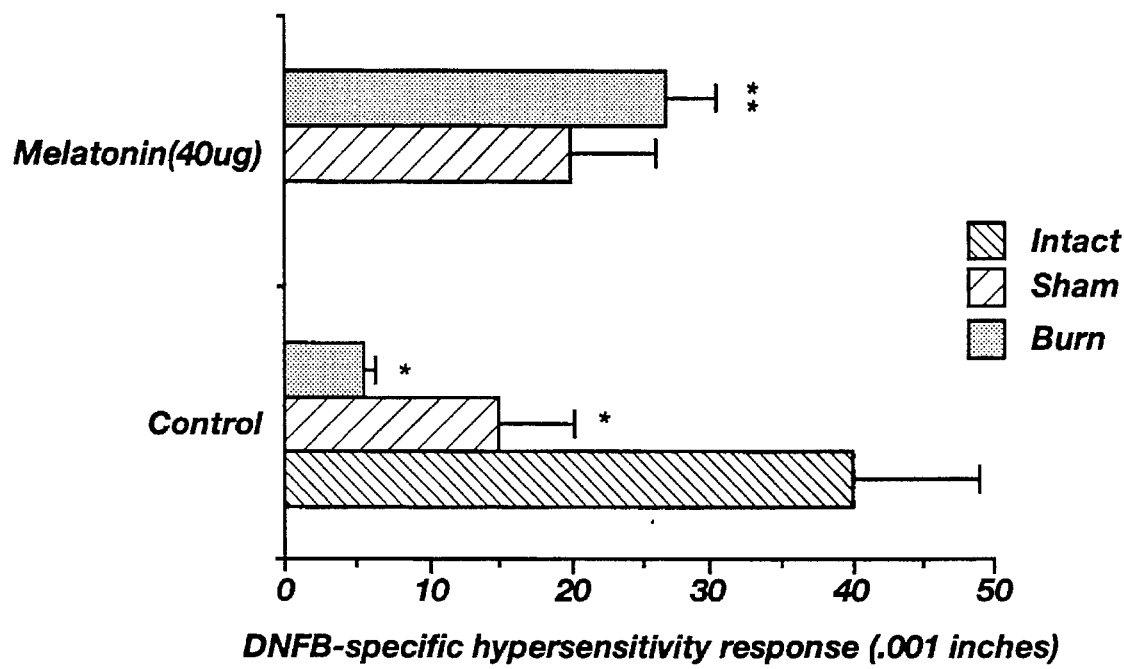
FIG. 1 is a bar diagram showing the effect of in vivo treatment with melatonin on contact sensitivity response as measured by footpad measurements.

Before the present method of stimulating post-trauma immune response in warm-blooded animals including humans is disclosed and described, it is to be understood that this invention is not limited to the particular process steps and materials disclosed herein as such process steps and materials may vary somewhat. It is also to be understood that the terminology used herein is used for the purpose of describing particular embodiments only and is not intended to be limiting since the scope of the present invention will be limited only by the appended claims and their equivalents.

In describing and claiming the present invention, the following terminology will be used in accordance with the definitions set out below.

As used herein, IL-2 is interleukin-2, IL-4 is interleukin-4, IL-6 is interleukin-6, and γ-IFN is γ-interferon.

As used herein, "warm-blooded animal" includes the human species.

As used herein, an "effective amount" of melatonin means a nontoxic but sufficient amount of melatonin to provide the desired effect and performance at a reasonable benefit/risk ratio attending any medical treatment. An "effective regimen" of exposure to light and dark means a sufficient amount of dark in a daily light/dark cycle to provide the desired effect.

As used herein, "traumatic injury" includes injury to a warm-blooded animal from exposure to high temperature resulting in thermal injury or burn, from surgery or transplantation, and from stress. These types of injury are representative and not intended to be a comprehensive list of what is covered by the term "traumatic injury."

Male Balb/c strain mice were obtained from the National Cancer Institute and housed in the pathogen-free University of Utah Vivarium rodent facility. The mice were rested for two weeks following shipment to the rodent facility before initiation of experiments. Age-matched mice housed together in groups of 4–6 mice, ranging in age from 8–10 weeks, were used in any single experiment. Separate groups of mice were assessed for contact sensitivity response and cytokine secretion. Scald burns (20–25% total body surface area) were given in a standardized manner according to J. Shelby & S. Merrell, *In Vivo Monitoring of Postburn Immune Response*, 27 J. Trauma 213 (1987), and J. Shelby & M. Krob, *Transfusion-induced Sensitization to Skin Allografts in Burned Mice*, 26 J. Trauma 54 (1986), which are hereby incorporated by reference. Full-thickness injury using this protocol was documented by histologic examination. Burn-injured mice were given intraperitoneal injections for fluid resuscitation of normal sterile saline. Two ml were given in the first 24 hours, followed by 1 ml on each of days 1 and 2. All animals, except some animals used in experiments on the effect of light/dark cycle on cytokine response, were maintained in a controlled environment with a standard 12 hour light/dark cycle (6 a.m. to 6 p.m. light, 6 p.m. to 6 a.m. dark). The light/dark cycle of animals housed under exceptions to this regimen will be described below. Sham stressed mice received identical treatment as described for injured mice, including depilation, saline and vehicle injections, and anesthesia, but were not injured. Intact controls for the cytokine analysis group were not handled until spleen harvest. Intact controls for the contact sensitivity response group were sensitized and challenged as will be described momentarily.

Melatonin (Sigma Chemical Co., St. Louis, Mo.) was dissolved in a minimal volume of ethanol and diluted with sterile phosphate-buffered saline (PBS) to a final 0.2% ethanol-PBS solution. The same ethanol-PBS solution was used as a vehicle in sham stressed mice. The melatonin was diluted to the appropriate concentration in PBS just before subcutaneous injection of 0.1 ml into the mice. Injection was at 4 p.m. daily. Although melatonin was administered by injection in the experiments described herein, the invention is not limited to administration by injection. Any effective method of administering melatonin is considered within the scope of the invention, including oral, transdermal, transmucosal, or other methods of administration now known or later developed. Melatonin is administered orally in humans, for example.

Contact Sensitivity

Mice were sensitized on 2 consecutive days (post burn days 1 and 2) with contact sensitizing antigen dinitrofluorobenzene (DNFB). A solution of 0.25% DNFB (Sigma Chemical Co., St. Louis, Mo.) was prepared in a 4:1 acetone-olive oil mixture, and 25 ml was applied to the shaved ventral surface. On post burn day 5, the contact sensitivity response was elicited by applying 10 ml of a challenge dose of the DNFB solution to the right hind footpads. The extent of swelling in all challenged mice, measured with an engineer's micrometer in $10^{-3}$ inches, was expressed as the difference in thickness between the challenged right hind footpad and unchallenged left hind footpad 24 hours after challenge (post burn day 6). Melatonin (40 μg/kg) was administered to the melatonin group at 4:00 p.m. daily starting the day of burn injury, until post burn day 6, when the foot pads were measured.

FIG. 1 shows the effect of in vivo treatment with melatonin on contact sensitivity response. The bars indicate the mean difference and standard error between challenged and unchallenged footpad measurements. The data show that contact sensitivity response was inhibited in untreated sham stressed and burn injured mice as compared to intact controls (the single asterisk signifies $p<0.05$ compared with intact control mice), as previously reported in B. Araneo et al., 128 Arch. Surg. 318 (1993). Sham stressed and injured mice receiving daily evening melatonin showed a significantly greater magnitude of contact hypersensitivity response (the double asterisk indicates $p<0.01$ compared with the untreated burn injured group), as compared to intact controls ($p<0.05$). These data indicate that melatonin administration enhanced the development of cell-mediated immune response to the contact antigen, DNFB, resulting in enhanced reactivity in sham stressed and burn injured mice.

Cytokine Secretion

Single cell suspensions of splenocytes harvested at day 5 post burn injury were prepared from spleens of control and experimental mice, washed twice in sterile balanced salt solution, and placed in culture in RPMI 1640 supplemented with 1% Nutridoma-NS (serum-free) (Boehringer Mannheim), antibiotics, 200 mM L-glutamine, and $5\times10^{-5}$M 2-mercaptoethanol, at a density of $1\times10^7$ cells/ml/well. Cells were cultured with and without 1.5 mg of the T-cell specific mitogen, anti-CD3e, in a 24-well cluster culture plate for 24 hours to induce cytokine release. Cell-free supernatants were collected and stored at 4° C. for quantitation of cytokine content. The culture conditions have previously been assessed as providing optimal conditions for evaluation of splenocyte cytokine secretion. R. Daynes et al, *Regulation of Murine Lymphokine Production In Vivo. III. The Lymphoid Microenvironment Exerts Regulatory Influences over T Helper Function*, 171 J. Exp. Med. 979 (1990).

Monoclonal antibodies used in these experiments were prepared from culture supernatants of appropriate B-cell hybridomas grown in serum-free conditions. The antibodies were from the following hybridoma clones: S4B6—rat antimurine IL-2; XMG1.2—rat anti-δ-interferon; 1452C-11.2—hamster antimurine CD3e; 11B11—rat antimurine IL-4; MP5-20F3—rat antimurine IL-6. Murine recombinant δ-interferon, IL-2, and IL-4, and human recombinant IL-6 were used as reference standards for bioassays and ELISA.

Figure 2A:
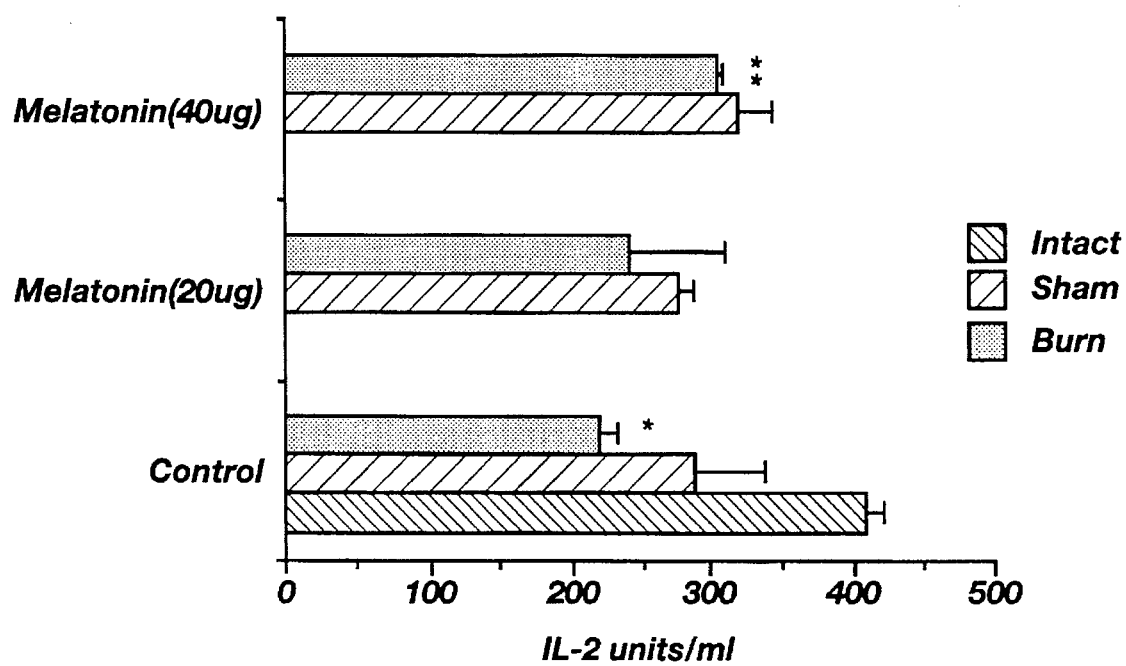
FIGS. 2A–D are bar diagrams showing the effect of in vivo treatment with melatonin on splenocyte secretion of IL-2 (FIG. 2A), IL-4 (FIG. 2B), $\delta$-IFN (FIG. 2C), and IL-6 (FIG. 2D).

For the exogenous melatonin experiment, both IL-2 and IL-4 production (FIGS. 2A and 2B) were assessed using a standard bioassay, as described in B. Araneo et al., *Administration of Dehydroepiandrosterone to Burned Mice Preserves Normal Immunologic Competence*, 128 Arch. Surg. 318 (1993), and hereby incorporated by reference. HT-2 cells were the indicator cell line, and IL-2 was distinguished from IL-4 by using either monoclonal anti-IL-2 or anti-IL-4 antibodies in the culture media, which was supplemented with Nutridoma-NS (serum-free). A modified MTT-based colorimetric assay was performed with spectrophotometric readings (O.D.) for each titration analyzed by least squares regression using a second-degree polynomial curve-fitting program to obtain a unit value to the interleukin under evaluation, with the mean and standard deviation reported.

Levels of IL-2 in the light/dark environment experiment (FIG. 3A) and all levels of IL-6 (FIGS. 2D and 3D) and δ-IFN (FIGS. 2C and 3C) were quantitated by capture ELISA, as described in B. Araneo et al., 128 Arch. Surg. 318 (1993), incorporated herein by reference. The appropriate capture antibody was adsorbed to the wells of a 96-well microtest plate. Test supernatants were diluted (1:10) and twofold serial dilutions of the appropriate reference cytokine were added to the wells, followed by biotinylated-detection antibody. The ELISA was developed using an avidin-horse-radish peroxidase conjugate and appropriate substrate. Optical density readings were taken at 405 nm using a 96-well microtest plate spectrophotometer. The lower limit of detection for most of these cytokines was less than 50 pg/ml.

Figure 2B:
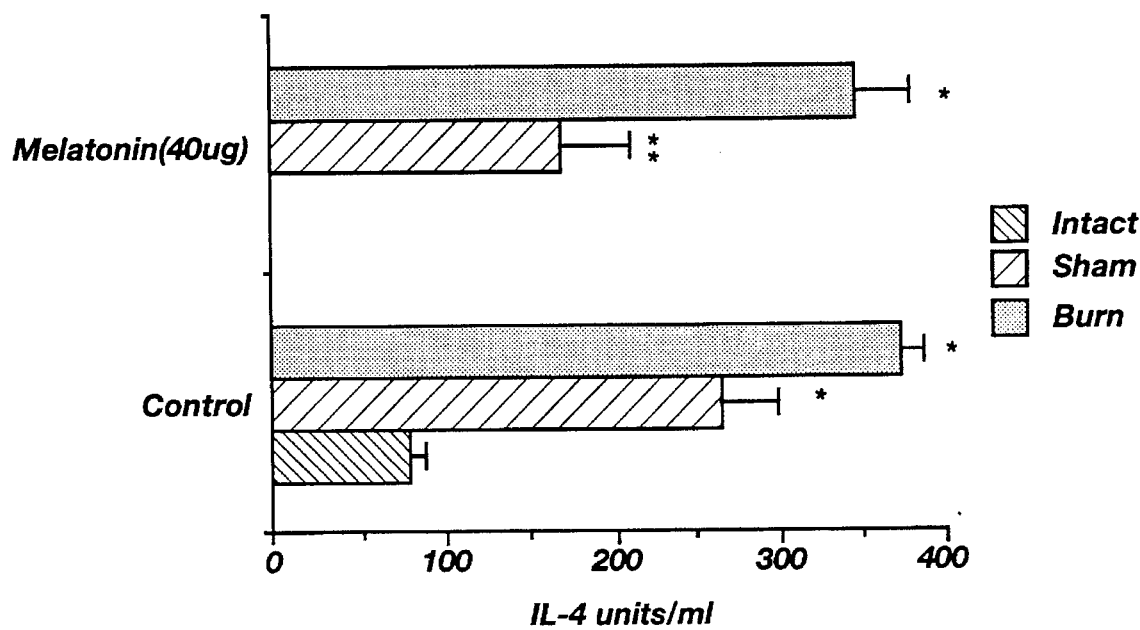
Figure 2C:
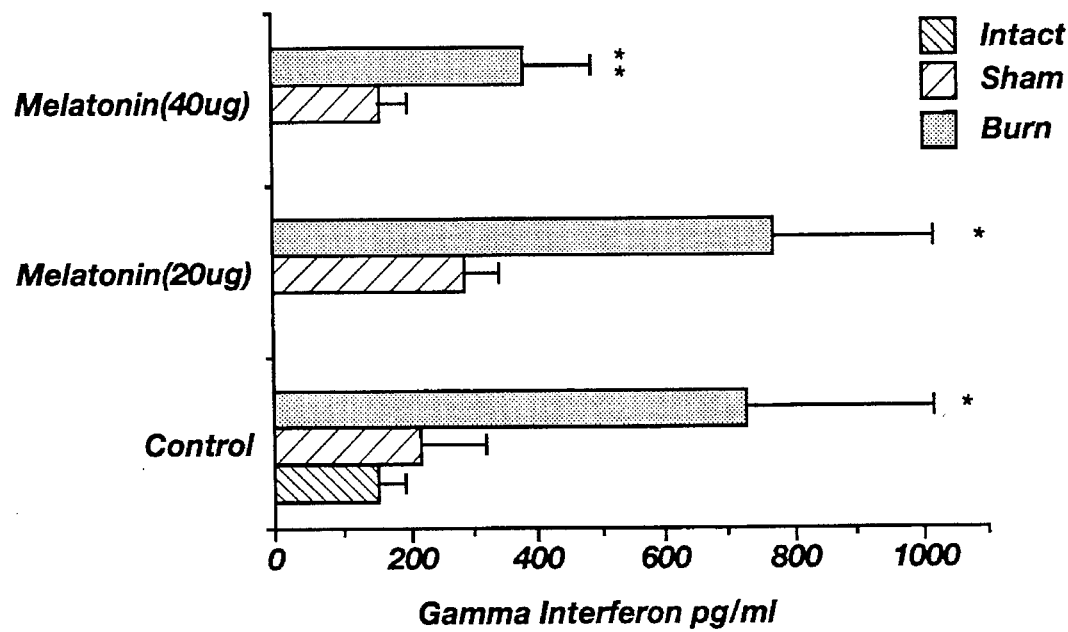
Figure 2D:
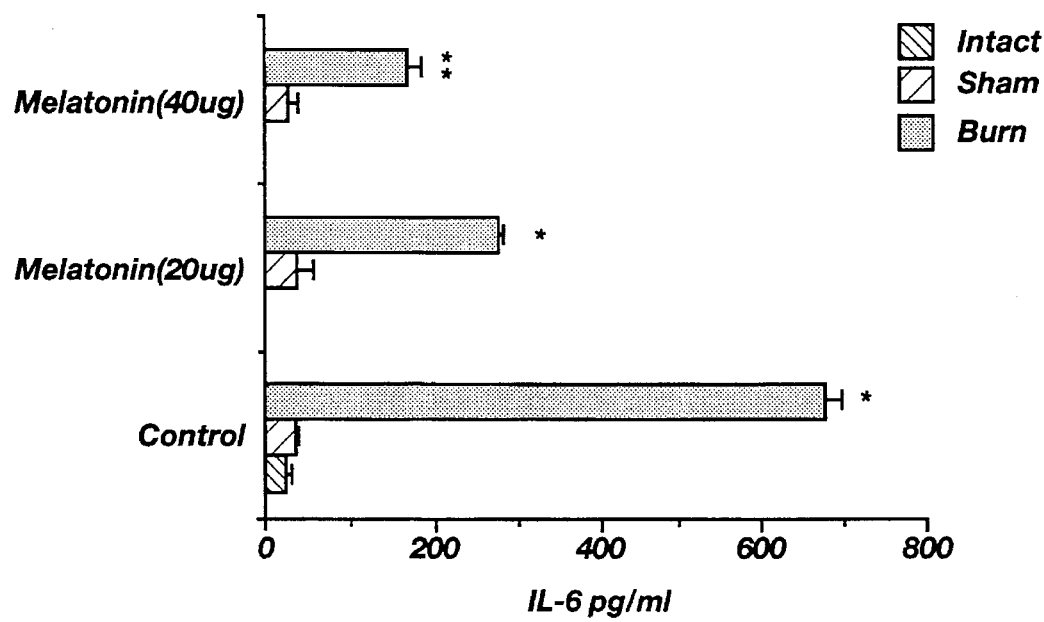

Anti-CD3e-stimulated splenocyte IL-2 secretion was reduced in sham stressed and thermally injured mice compared to intact controls (FIG. 2A; * signifies $p<0.01$ compared with intact control), while IL-4 levels were increased (FIG. 2B; * signifies $p<0.001$ compared with intact control;  signifies $p<0.05$ compared with intact control). Melatonin (20 μg/kg or 40 μg/kg) was given daily, starting on the day of injury through post burn day 4, with splenocyte harvest on post burn day 5. Thermally injured mice receiving evening melatonin at the concentration of 40 μg/kg showed increased splenocyte secretion of IL-2 (FIG. 2A;  signifies $p<0.01$ compared with burn control), with no change observed in IL-4 levels (FIG. 2B). These results indicate that in vivo exogenous melatonin therapy increased the potential for IL-2 secretion by stimulated splenocytes from sham stressed and burn injured mice, while having little or no effect on IL-4 secretion in this population of cells.

In contrast to depressed IL-2 secretion observed in supernatants from stimulated splenocytes from burn injured Balb/c mice, spontaneous secretion of δ-IFN (FIG. 2C; * signifies $p<0.05$ compared with intact control) and IL-6 (FIG. 2D; * signifies $p<0.001$ compared with sham and intact controls) by unstimulated splenocytes from these mice was increased at post burn day 5 in comparison with spontaneous splenocyte secretion of these cytokines from sham stressed and intact control mice. Secretion of δ-IFN was reduced in thermally injured mice receiving 40 μg/kg evening melatonin (FIG. 2C;  signifies $p<0.05$ compared with burn control). Similarly, splenocyte production of IL-6 was significantly reduced in thermally injured mice receiving 20 μg/kg and 40 μg/kg evening melatonin (FIG. 2D;  signifies $p<0.001$ compared with burn control).

Thus, administration of exogenous melatonin was effective in regulating cytokine secretion following burn injury. Specifically, depressed levels of secretion of IL-2 following burn injury were increased, and elevated levels of IL-6 and δ-IFN following thermal injury were decreased in response to administered melatonin. Little or no apparent effect on secretion of IL-4 by melatonin was observed.

Effect of Light/Dark Cycle on Cytokine Secretion

Male Balb/c mice were burn injured and given saline intraperitoneal resuscitation as described above. Immediately afterward, the mice were placed in a 12 hour normal light/dark cycle (NLD; 6:00 a.m. to 6:00 p.m. light and 6:00 p.m. to 6:00 a.m. dark) or a 24 hour dark environment (DD). For each light/dark cycle environment there were control, sham, and burn injured groups. At post burn day 5, the mice were euthanized and the spleens were removed for cytokine analysis as described above. Splenocytes were placed in culture, and the supernatants were harvested for cytokine analysis by ELISA as described above.

Figure 3A:
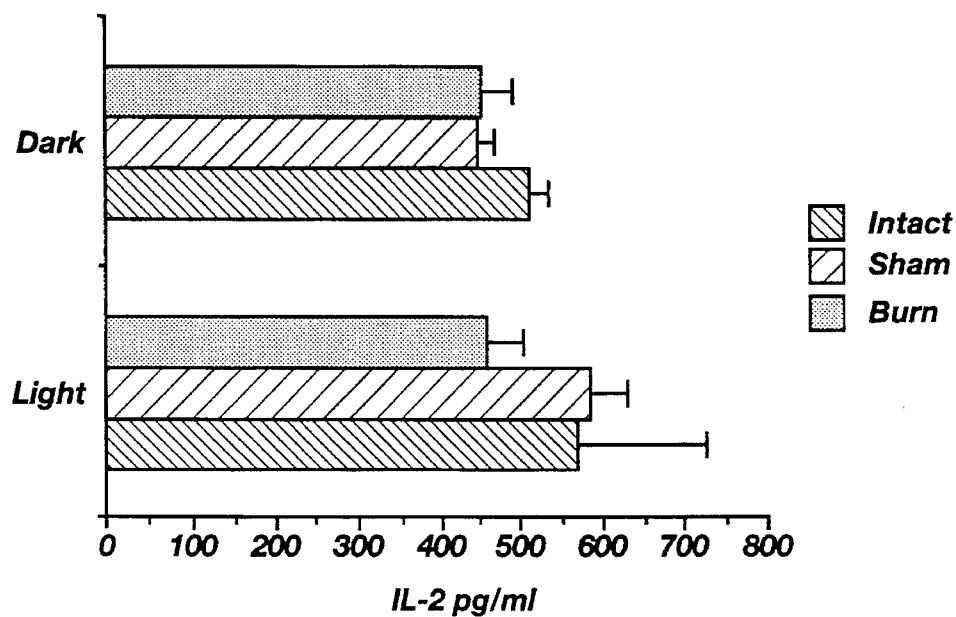
FIGS. 3A–D are bar diagrams showing the effect of light/dark cycle on splenocyte secretion of IL-2 (FIG. 3A), IL-4 (FIG. 3B); $\gamma$-IFN (FIG. 3C), and IL-6 (FIG. 3D).
Figure 3B:
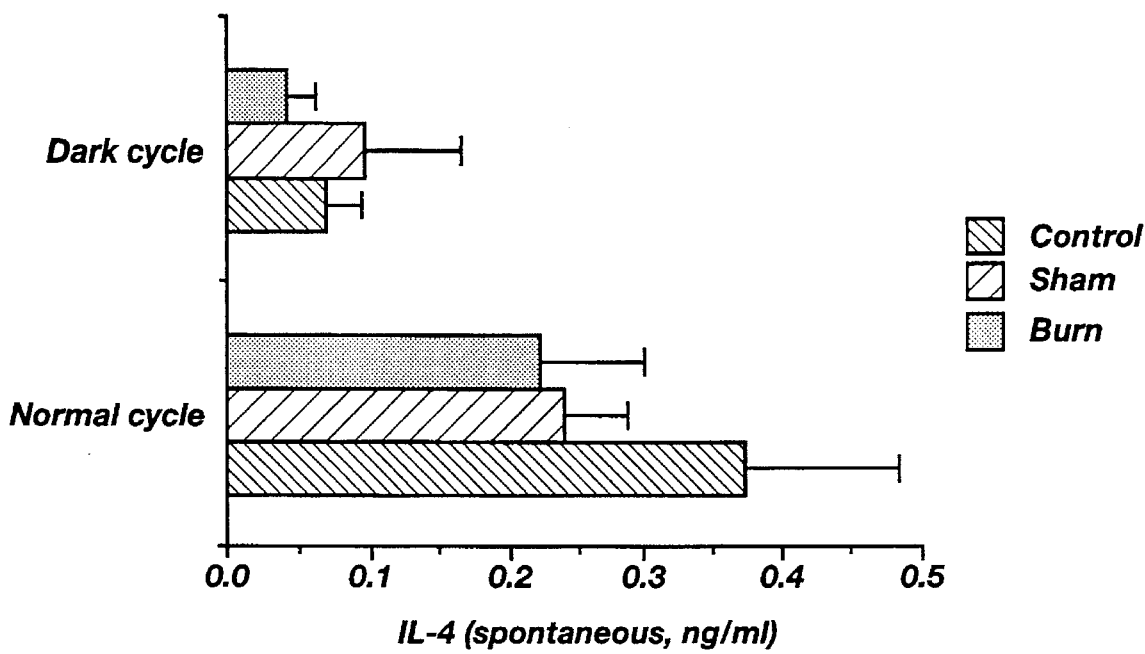
Figure 3C:
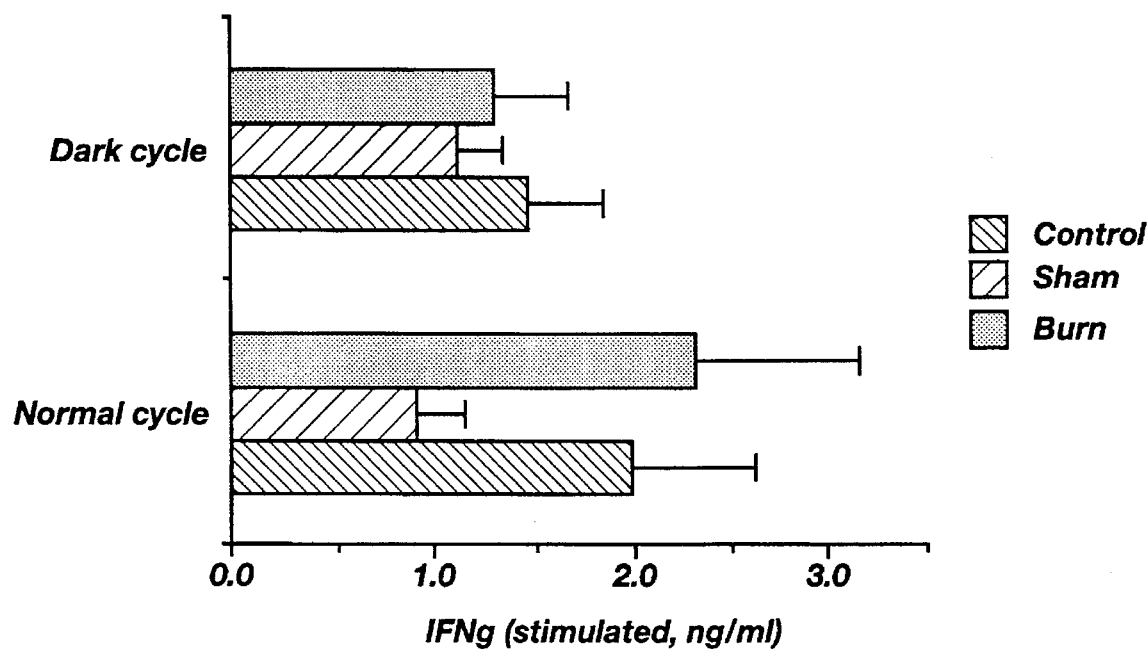
Figure 3D:
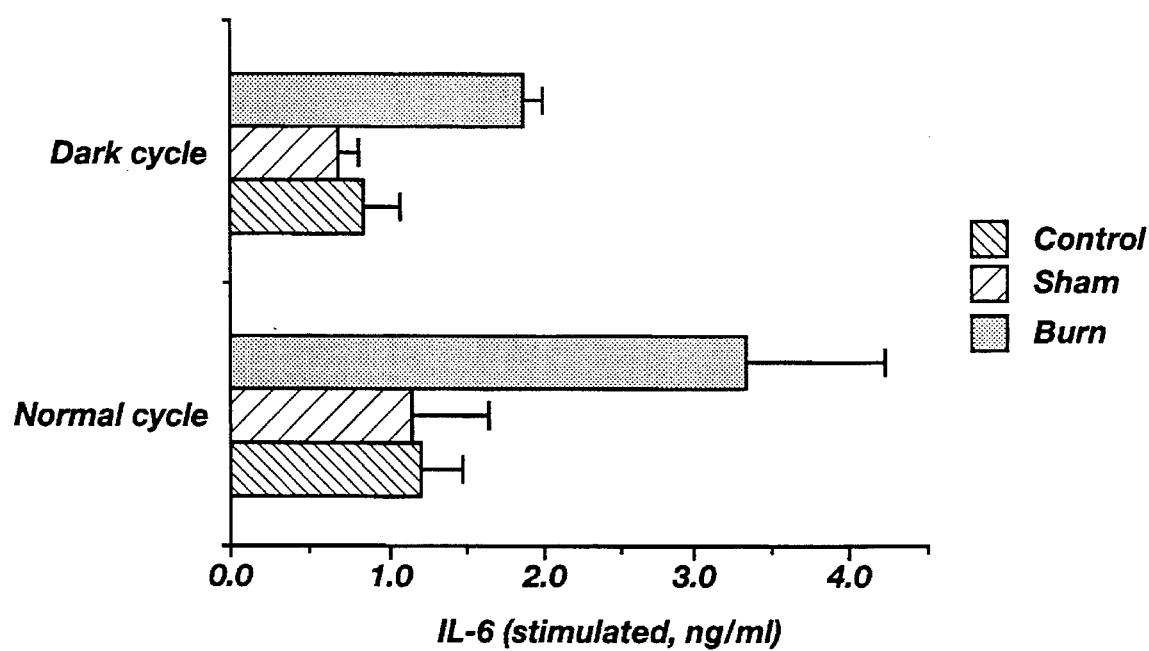

FIG. 3A shows that there was no difference in splenocyte IL-2 production between NLD and DD environments in any of the groups. In contrast, IL-4 production (FIG. 3B) was markedly reduced in the DD burn injured group, as compared to the NLD burn groups ($p<0.05$). Similarly, δ-IFN levels (FIGS. 3C) were lower in the burn injured group in the DD environment ($p<0.01$). Production of IL-6 (FIG. 3D) was significantly increased in the NLD burn injured mice, as compared to NLD control and sham animals, while IL-6 levels in splenocyte cultures from DD burn injured animals were not increased ($p<0.001$).

Thus, alterations in the light/dark cycle for burn injured mice appear to modify patterns of splenocyte cytokine production in a manner similar to that observed following post burn administration of melatonin. The light/dark cycle environment appears to play a role in regulation of cytokine production after burn injury, probably through a pathway involving melatonin production.

A combination of administration of melatonin and regulation of light/dark cycle can also be used advantageously to enhance the immune response. This is relevant to the situation of burn patients in intensive care units, for example, who are exposed to virtually continuous light. Not only does the traumatic injury decrease the amount of circulating melatonin in such a patient's body, thus depressing the immune system, but the exposure to excess light also depresses the immune system. Thus, regulation of the light/dark cycle to provide an effective regimen of exposure to light and dark and administration of an effective dose of melatonin can work together to enhance functioning of the immune system.

We claim:

1. A method of decreasing elevated levels of IL-6 and δ-IFN that are secreted in response to thermal injury in a warm-blooded animal, comprising the step of daily administering an effective amount of melatonin to said warm-blooded animal.

2. The method of claim 1 wherein said step comprises injecting said effective amount of melatonin into said warm-blooded animal.

3. The method of claim 1 wherein said step comprises administering said effective amount by a route selected from the group consisting of oral, transdermal, and transmucosal.

4. The method of claim 1 wherein said melatonin is administered so as to provide a peak amount of circulating melatonin at a time in said animal's daily cycle to coincide with a time when endogenous melatonin reaches peak amounts.

5. A method of decreasing elevated levels of IL-6 and δ-IFN that are secreted in response to thermal injury in a warm-blooded animal; comprising the step of administering an effective regimen of exposure to a member selected from the group consisting of dark and combinations of light and dark.

6. The method of claim 5 wherein said regimen is daily exposure to 24 hours of dark.

7. The method of claim 5 wherein said step further comprises daily administering an effective amount of melatonin to said warm-blooded animal.

8. The method of claim 7 wherein said melatonin is administered by injection.

9. The method of claim 7 wherein said melatonin is administered by a route selected from the group consisting of oral, transdermal, and transmucosal.

10. The method of claim 7 wherein said melatonin is administered so as to provide a peak amount of circulating melatonin at a time in said animal's daily cycle to coincide with a time when endogenous melatonin reaches peak amounts.

* * * * *